(12) United States Patent
Miyagawa et al.

(10) Patent No.: US 9,175,064 B2
(45) Date of Patent: Nov. 3, 2015

(54) HLA-E CHIMERIC MOLECULE

(76) Inventors: Shuji Miyagawa, Ashiya (JP);
Katsuyoshi Matsunami, Hiroshima (JP)

( * ) Notice: Subject to any disclaimer, the term of this patent is extended or adjusted under 35 U.S.C. 154(b) by 2387 days.

(21) Appl. No.: 10/578,139

(22) PCT Filed: Nov. 4, 2004

(86) PCT No.: PCT/JP2004/016776
§ 371 (c)(1),
(2), (4) Date: Jul. 17, 2006

(87) PCT Pub. No.: WO2005/042693
PCT Pub. Date: May 12, 2005

(65) Prior Publication Data
US 2007/0259403 A1    Nov. 8, 2007

(30) Foreign Application Priority Data
Nov. 4, 2003   (JP) ................. 2003-374944

(51) Int. Cl.
*C07K 14/74* (2006.01)
*C12N 15/12* (2006.01)

(52) U.S. Cl.
CPC ....... *C07K 14/70539* (2013.01); *A01K 2267/02* (2013.01); *C07K 2319/00* (2013.01)

(58) Field of Classification Search
None
See application file for complete search history.

(56) References Cited

PUBLICATIONS

Matsunami et al (Transplantation, 78(2), p. 157, Abstract O401, Jul. 27, 2004).*
Strong et al (J. Biol. Chem. Feb. 14, 2003, 278(7): 5082-5090).*
Matsunami et al (BBRC, 2006, 347: 692-697).*

* cited by examiner

*Primary Examiner* — Gerald R Ewoldt
*Assistant Examiner* — Marianne Dibrino
(74) *Attorney, Agent, or Firm* — Birch, Stewart, Kolasch & Birch, LLP

(57) ABSTRACT

HLA-E chimeric molecules for providing nonhuman mammalian cells resistant to cytotoxic human NK cells, nucleotide sequences encoding these chimeric molecules, and nonhuman mammalian cells and nonhuman mammals transformed with such nucleotide sequences are disclosed herein. The HLA-E chimeric molecules of the invention contain a peptide that reforms all or part of the signal peptide region, α1 domain and/or α2 domain of HLA-E, and a nucleotide sequence of the invention encodes a HLA-E chimeric molecule. A transformant incorporating a nucleotide sequence of the invention expresses HLA-E efficiently.

1 Claim, No Drawings

SEQUENCE LISTING

```
<160> NUMBER OF SEQ ID NOS: 92

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      chimeric sequence SP of HLA-E

<400> SEQUENCE: 1

Met Val Asp Gly Thr Leu Leu Leu Leu Ser Glu Ala Leu Ala Leu
1               5                   10                  15

Thr Gln Thr Trp Ala
            20

<210> SEQ ID NO 2
<211> LENGTH: 90
<212> TYPE: PRT
```

<213> ORGANISM: Artificial Sequence
<220> FEATURE:
<223> OTHER INFORMATION: Description of Artificial Sequence: Synthetic chimeric sequence a1 domain of HLA-E

<400> SEQUENCE: 2

```
Gly Ser His Ser Leu Lys Tyr Phe His Thr Ser Val Ser Arg Pro Gly
 1               5                  10                  15

Arg Gly Glu Pro Arg Phe Ile Ser Val Gly Tyr Val Asp Asp Thr Gln
            20                  25                  30

Phe Val Arg Phe Asp Asn Asp Ala Ala Ser Pro Arg Met Val Pro Arg
        35                  40                  45

Ala Pro Trp Met Glu Gln Glu Gly Ser Glu Tyr Trp Asp Arg Glu Thr
    50                  55                  60

Arg Ser Ala Arg Asp Thr Ala Gln Ile Phe Arg Val Asn Leu Arg Thr
65                  70                  75                  80

Leu Arg Gly Tyr Tyr Asn Gln Ser Glu Ala
                85                  90
```

<210> SEQ ID NO 3
<211> LENGTH: 92
<212> TYPE: PRT
<213> ORGANISM: Artificial Sequence
<220> FEATURE:
<223> OTHER INFORMATION: Description of Artificial Sequence: Synthetic chimeric sequence a2 domain of HLA-E

<400> SEQUENCE: 3

```
Gly Ser His Thr Leu Gln Trp Met His Gly Cys Glu Leu Gly Pro Asp
 1               5                  10                  15

Arg Arg Phe Leu Arg Gly Tyr Glu Gln Phe Ala Tyr Asp Gly Lys Asp
            20                  25                  30

Tyr Leu Thr Leu Asn Glu Asp Leu Arg Ser Trp Thr Ala Val Asp Thr
        35                  40                  45

Ala Ala Gln Ile Ser Glu Gln Lys Ser Asn Asp Ala Ser Glu Ala Glu
    50                  55                  60

His Gln Arg Ala Tyr Leu Glu Asp Thr Cys Val Glu Trp Leu His Lys
65                  70                  75                  80

Tyr Leu Glu Lys Gly Lys Glu Thr Leu Leu His Leu
                85                  90
```

<210> SEQ ID NO 4
<211> LENGTH: 92
<212> TYPE: PRT
<213> ORGANISM: Artificial Sequence
<220> FEATURE:
<223> OTHER INFORMATION: Description of Artificial Sequence: Synthetic chimeric sequence a3 domain of HLA-E

<400> SEQUENCE: 4

```
Glu Pro Pro Lys Thr His Val Thr His His Pro Ile Ser Asp His Glu
 1               5                  10                  15

Ala Thr Leu Arg Cys Trp Ala Leu Gly Phe Tyr Pro Ala Glu Ile Thr
            20                  25                  30

Leu Thr Trp Gln Gln Asp Gly Glu Gly His Thr Gln Asp Thr Glu Leu
        35                  40                  45

Val Glu Thr Arg Pro Ala Gly Asp Gly Thr Phe Gln Lys Trp Ala Ala
    50                  55                  60

Val Val Val Pro Ser Gly Glu Glu Gln Arg Tyr Thr Cys His Val Gln
65                  70                  75                  80
```

```
His Glu Gly Leu Pro Glu Pro Val Thr Leu Arg Trp
            85                  90
```

<210> SEQ ID NO 5
<211> LENGTH: 63
<212> TYPE: PRT
<213> ORGANISM: Artificial Sequence
<220> FEATURE:
<223> OTHER INFORMATION: Description of Artificial Sequence:
      Synthetic chimeric sequence Transmembrane domain of HLA-E

<400> SEQUENCE: 5

```
Lys Pro Ala Ser Gln Pro Thr Ile Pro Ile Val Gly Ile Ile Ala Gly
1               5                   10                  15

Leu Val Leu Leu Gly Ser Val Val Ser Gly Ala Val Val Ala Ala Val
            20                  25                  30

Ile Trp Arg Lys Lys Ser Ser Gly Gly Lys Gly Gly Ser Tyr Ser Lys
        35                  40                  45

Ala Glu Trp Ser Asp Ser Ala Gln Gly Ser Glu Ser His Ser Leu
    50                  55                  60
```

<210> SEQ ID NO 6
<211> LENGTH: 63
<212> TYPE: DNA
<213> ORGANISM: Artificial Sequence
<220> FEATURE:
<223> OTHER INFORMATION: Description of Artificial Sequence:
      Synthetic chimeric sequence SP of HLA-E

<400> SEQUENCE: 6

```
atggtagatg gaaccctcct tttactcctc tcggaggccc tggcccttac ccagacctgg    60
gcg                                                                  63
```

<210> SEQ ID NO 7
<211> LENGTH: 270
<212> TYPE: DNA
<213> ORGANISM: Artificial Sequence
<220> FEATURE:
<223> OTHER INFORMATION: Description of Artificial Sequence:
      Synthetic chimeric sequence a1 domain of HLA-E

<400> SEQUENCE: 7

```
ggctcccact ccttgaagta tttccacact tccgtgtccc ggcccggccg cggggagccc    60
cgcttcatct ctgtgggcta cgtggacgac acccagttcg tgcgcttcga caacgacgcc   120
gcgagtccga ggatggtgcc gcgggcgccg tggatggagc aggagggtc agagtattgg    180 gaccgggaga cacggagcgc cagggacacc gcacagattt ccgagtgaa tctgcggacg    240 ctgcgcggct actacaatca gagcgaggcc                                    270
```

<210> SEQ ID NO 8
<211> LENGTH: 276
<212> TYPE: DNA
<213> ORGANISM: Artificial Sequence
<220> FEATURE:
<223> OTHER INFORMATION: Description of Artificial Sequence:
      Synthetic chimeric sequence a2 domain of HLA-E

<400> SEQUENCE: 8

```
gggtctcaca ccctgcagtg gatgcatggc tgcgagctgg ggcccgacag gcgcttcctc    60
cgcgggtatg aacagttcgc ctacgacggc aaggattatc tcaccctgaa tgaggacctg   120
cgctcctgga ccgcggtgga cacggcggct cagatctccg agcaaaagtc aaatgatgcc   180
```

```
tctgaggcgg agcaccagag agcctacctg aagacacat gcgtggagtg gctccacaaa    240
tacctggaga aggggaagga gacgctgctt cacctg                              276
```

<210> SEQ ID NO 9
<211> LENGTH: 276
<212> TYPE: DNA
<213> ORGANISM: Artificial Sequence
<220> FEATURE:
<223> OTHER INFORMATION: Description of Artificial Sequence:
      Synthetic chimeric sequence a3 domain of HLA-E

<400> SEQUENCE: 9

```
gagcccccaa agacacacgt gactcaccac cccatctctg accatgaggc caccctgagg     60
tgctgggccc tgggcttcta ccctgcggag atcacactga cctggcagca ggatggggag    120
ggccataccc aggacacgga gctcgtggag accaggcctg caggggatgg aaccttccag    180
aagtgggcag ctgtggtggt gccttctgga gaggagcaga gatacacgtg ccatgtgcag    240
catgaggggc tacccgagcc cgtcaccctg agatgg                              276
```

<210> SEQ ID NO 10
<211> LENGTH: 192
<212> TYPE: DNA
<213> ORGANISM: Artificial Sequence
<220> FEATURE:
<223> OTHER INFORMATION: Description of Artificial Sequence:
      Synthetic chimeric sequence Transmembrane domain of HLA-E

<400> SEQUENCE: 10

```
aagccggctt cccagcccac catccccatc gtgggcatca ttgctggcct ggttctcctt     60
ggatctgtgg tctctggagc tgtggttgct gctgtgatat ggaggaagaa gagctcaggt    120
ggaaaaggag ggagctactc taaggctgag tggagcgaca gtgcccaggg gtctgagtct    180
cacagcttgt aa                                                        192
```

<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence: Synthetic
      chimeric sequence SP of HLA-G1

<400> SEQUENCE: 11

```
Met Val Val Met Ala Pro Arg Thr Leu Phe Leu Leu Leu Ser Gly Ala
1               5                   10                  15

Leu Thr Leu Thr Glu Thr Trp Ala
            20
```

<210> SEQ ID NO 12
<211> LENGTH: 90
<212> TYPE: PRT
<213> ORGANISM: Artificial Sequence
<220> FEATURE:
<223> OTHER INFORMATION: Description of Artificial Sequence:
      Synthetic chimeric sequence a1 domain of HLA-G1

<400> SEQUENCE: 12

```
Gly Ser His Ser Met Arg Tyr Phe Ser Ala Ala Val Ser Arg Pro Gly
1               5                   10                  15

Arg Gly Glu Pro Arg Phe Ile Ala Met Gly Tyr Val Asp Asp Thr Gln
            20                  25                  30
```

```
Phe Val Arg Phe Asp Ser Asp Ser Ala Cys Pro Arg Met Glu Pro Arg
            35                  40                  45

Ala Pro Trp Val Glu Gln Glu Gly Pro Glu Tyr Trp Glu Glu Glu Thr
 50                  55                  60

Arg Asn Thr Lys Ala His Ala Gln Thr Asp Arg Met Asn Leu Gln Thr
 65                  70                  75                  80

Leu Arg Gly Tyr Tyr Asn Gln Ser Glu Ala
                 85                  90

<210> SEQ ID NO 13
<211> LENGTH: 92
<212> TYPE: PRT
<213> ORGANISM: Artificial Sequence
<220> FEATURE:
<223> OTHER INFORMATION: Description of Artificial Sequence:
      Synthetic chimeric sequence a2 domain of HLA-G1

<400> SEQUENCE: 13

Ser Ser His Thr Leu Gln Trp Met Ile Gly Cys Asp Leu Gly Ser Asp
 1               5                  10                  15

Gly Arg Leu Leu Arg Gly Tyr Glu Gln Tyr Ala Tyr Asp Gly Lys Asp
                 20                  25                  30

Tyr Leu Ala Leu Asn Glu Asp Leu Arg Ser Trp Thr Ala Ala Asp Thr
            35                  40                  45

Ala Ala Gln Ile Ser Lys Arg Lys Cys Glu Ala Ala Asn Val Ala Glu
 50                  55                  60

Gln Arg Arg Ala Tyr Leu Glu Gly Thr Cys Val Glu Trp Leu His Arg
 65                  70                  75                  80

Tyr Leu Glu Asn Gly Lys Glu Met Leu Gln Arg Ala
                 85                  90

<210> SEQ ID NO 14
<211> LENGTH: 92
<212> TYPE: PRT
<213> ORGANISM: Artificial Sequence
<220> FEATURE:
<223> OTHER INFORMATION: Description of Artificial Sequence:
      Synthetic chimeric sequence a3 domain of HLA-G1

<400> SEQUENCE: 14

Asp Pro Pro Lys Thr His Val Thr His His Pro Val Phe Asp Tyr Glu
 1               5                  10                  15

Ala Thr Leu Arg Cys Trp Ala Leu Gly Phe Tyr Pro Ala Glu Ile Ile
                 20                  25                  30

Leu Thr Trp Gln Arg Asp Gly Glu Asp Gln Thr Gln Asp Val Glu Leu
            35                  40                  45

Val Glu Thr Arg Pro Ala Gly Asp Gly Thr Phe Gln Lys Trp Ala Ala
 50                  55                  60

Val Val Val Pro Ser Gly Glu Glu Gln Arg Tyr Thr Cys His Val Gln
 65                  70                  75                  80

His Glu Gly Leu Pro Glu Pro Leu Met Leu Arg Trp
                 85                  90

<210> SEQ ID NO 15
<211> LENGTH: 40
<212> TYPE: PRT
<213> ORGANISM: Artificial Sequence
<220> FEATURE:
<223> OTHER INFORMATION: Description of Artificial Sequence:
      Synthetic chimeric sequence Transmembrane domain of HLA-G1
```

-continued

<400> SEQUENCE: 15

Lys Gln Ser Ser Leu Pro Thr Ile Pro Ile Met Gly Ile Val Ala Gly
1               5                   10                  15

Leu Val Leu Ala Ala Val Val Thr Gly Ala Ala Val Ala Ala Val
            20                  25                  30

Leu Trp Arg Lys Lys Ser Ser Asp
        35                  40

<210> SEQ ID NO 16
<211> LENGTH: 72
<212> TYPE: DNA
<213> ORGANISM: Artificial Sequence
<220> FEATURE:
<223> OTHER INFORMATION: Description of Artificial Sequence: Synthetic
      chimeric sequence SP of HLA-G1

<400> SEQUENCE: 16
atggtggtca tggcgcccg aaccctcttc ctgctgctct cgggggccct gaccctgacc      60
gagacctggg cg                                                         72

<210> SEQ ID NO 17
<211> LENGTH: 270
<212> TYPE: DNA
<213> ORGANISM: Artificial Sequence
<220> FEATURE:
<223> OTHER INFORMATION: Description of Artificial Sequence: Synthetic
      chimeric sequence a1 domain of HLA-G1

<400> SEQUENCE: 17
ggctcccact ccatgaggta tttcagcgcc gccgtgtccc ggcccggccg cggggagccc      60
cgcttcatcg ccatgggcta cgtggacgac acgcagttcg tgcggttcga cagcgactcg     120
gcgtgtccga ggatggagcc gcgggcgccg tgggtggagc aggaggggcc agagtattgg     180
gaagaggaga cacggaacac caaggcccac gcacagactg acagaatgaa cctgcagacc     240
ctgcgcggct actacaacca gagcgaggcc                                     270

<210> SEQ ID NO 18
<211> LENGTH: 276
<212> TYPE: DNA
<213> ORGANISM: Artificial Sequence
<220> FEATURE:
<223> OTHER INFORMATION: Description of Artificial Sequence: Synthetic
      chimeric sequence a2 domain of HLA-G1

<400> SEQUENCE: 18
agttctcaca ccctccagtg gatgattggc tgcgacctgg ggtccgacgg tcgcctcctc      60
cgcgggtatg aacagtatgc ctacgatggc aaggattacc tcgccctgaa cgaggacctg     120
cgctcctgga ccgcagcgga cactgcggct cagatctcca agcgcaagtg tgaggcggcc     180
aatgtggctg aacaaaggag agcctacctg gagggcacgt gcgtggagtg gctccacaga     240
tacctggaga cgggaaggaa gatgctgcag cgcgcg                               276

<210> SEQ ID NO 19
<211> LENGTH: 276
<212> TYPE: DNA
<213> ORGANISM: Artificial Sequence
<220> FEATURE:
<223> OTHER INFORMATION: Description of Artificial Sequence: Synthetic
      chimeric sequence a3 domain of HLA-G1

<400> SEQUENCE: 19

```
gaccccccca agacacacgt gacccaccac cctgtctttg actatgaggc caccctgagg    60
tgctgggccc tgggcttcta ccctgcggag atcatactga cctggcagcg ggatggggag   120
gaccagaccc aggacgtgga gctcgtggag accaggcctg caggggatgg aaccttccag   180
aagtgggcag ctgtggtggt gccttctgga gaggagcaga gatacacgtg ccatgtgcag   240 catgagggc tgccggagcc cctcatgctg agatgg                              276
```

```
<210> SEQ ID NO 20
<211> LENGTH: 123
<212> TYPE: DNA
<213> ORGANISM: Artificial Sequence
<220> FEATURE:
<223> OTHER INFORMATION: Description of Artificial Sequence: Synthetic
      chimeric sequence Transmembrane domain of HLA-G1

<400> SEQUENCE: 20
```

```
aagcagtctt ccctgcccac catccccatc atgggtatcg ttgctggcct ggttgtcctt    60
gcagctgtag tcactggagc tgcggtcgct gctgtgctgt ggagaaagaa gagctcagat   120
tga                                                                 123
```

```
<210> SEQ ID NO 21
<211> LENGTH: 24
<212> TYPE: PRT
<213> ORGANISM: Artificial Sequence
<220> FEATURE:
<223> OTHER INFORMATION: Description of Artificial Sequence: Synthetic
      chimeric sequence Reformed SP

<400> SEQUENCE: 21
```

Met Ala Val Met Ala Pro Arg Thr Leu Val Leu Leu Leu Ser Gly Ala
1               5                  10                  15

Leu Thr Leu Thr Glu Thr Trp Ala
            20

```
<210> SEQ ID NO 22
<211> LENGTH: 90
<212> TYPE: PRT
<213> ORGANISM: Artificial Sequence
<220> FEATURE:
<223> OTHER INFORMATION: Description of Artificial Sequence: Synthetic
      chimeric sequence a1 domain

<400> SEQUENCE: 22
```

Gly Ser His Ser Leu Lys Tyr Phe His Thr Ser Val Ser Arg Pro Gly
1               5                  10                  15

Arg Gly Glu Pro Arg Phe Ile Ser Val Gly Tyr Val Asp Asp Thr Gln
            20                  25                  30

Phe Val Arg Phe Asp Asn Asp Ala Ala Ser Pro Arg Met Val Pro Arg
        35                  40                  45

Ala Pro Trp Met Glu Gln Glu Gly Ser Glu Tyr Trp Asp Arg Glu Thr
    50                  55                  60

Arg Ser Ala Arg Asp Thr Ala Gln Ile Phe Arg Val Asn Leu Arg Thr
65                  70                  75                  80

Leu Arg Gly Tyr Tyr Asn Gln Ser Glu Ala
                85                  90

```
<210> SEQ ID NO 23
<211> LENGTH: 92
<212> TYPE: PRT
<213> ORGANISM: Artificial Sequence
<220> FEATURE:
```

<223> OTHER INFORMATION: Description of Artificial Sequence: Synthetic
chimeric sequence a2 domain

<400> SEQUENCE: 23

Ser Ser His Thr Leu Gln Trp Met Ile Gly Cys Asp Leu Gly Ser Asp
1               5                   10                  15

Gly Arg Leu Leu Arg Gly Tyr Glu Gln Tyr Ala Tyr Asp Gly Lys Asp
            20                  25                  30

Tyr Leu Ala Leu Asn Glu Asp Leu Arg Ser Trp Thr Ala Ala Asp Thr
        35                  40                  45

Ala Ala Gln Ile Ser Lys Arg Lys Cys Glu Ala Ala Asn Val Ala Glu
    50                  55                  60

Gln Arg Arg Ala Tyr Leu Glu Gly Thr Cys Val Glu Trp Leu His Arg
65                  70                  75                  80

Tyr Leu Glu Asn Gly Lys Glu Met Leu Gln Arg Ala
                85                  90

<210> SEQ ID NO 24
<211> LENGTH: 92
<212> TYPE: PRT
<213> ORGANISM: Artificial Sequence
<220> FEATURE:
<223> OTHER INFORMATION: Description of Artificial Sequence:
    Synthetic chimeric sequence a3 domain

<400> SEQUENCE: 24

Glu Pro Pro Lys Thr His Val Thr His His Pro Ile Ser Asp His Glu
1               5                   10                  15

Ala Thr Leu Arg Cys Trp Ala Leu Gly Phe Tyr Pro Ala Glu Ile Thr
            20                  25                  30

Leu Thr Trp Gln Gln Asp Gly Glu Gly His Thr Gln Asp Thr Glu Leu
        35                  40                  45

Val Glu Thr Arg Pro Ala Gly Asp Gly Thr Phe Gln Lys Trp Ala Ala
    50                  55                  60

Val Val Val Pro Ser Gly Glu Glu Gln Arg Tyr Thr Cys His Val Gln
65                  70                  75                  80

His Glu Gly Leu Pro Glu Pro Val Thr Leu Arg Trp
                85                  90

<210> SEQ ID NO 25
<211> LENGTH: 63
<212> TYPE: PRT
<213> ORGANISM: Artificial Sequence
<220> FEATURE:
<223> OTHER INFORMATION: Description of Artificial Sequence:
    Synthetic chimeric sequence Transmembrane domain

<400> SEQUENCE: 25

Lys Pro Ala Ser Gln Pro Thr Ile Pro Ile Val Gly Ile Ile Ala Gly
1               5                   10                  15

Leu Val Leu Leu Gly Ser Val Val Ser Gly Ala Val Val Ala Ala Val
            20                  25                  30

Ile Trp Arg Lys Lys Ser Ser Gly Gly Lys Gly Gly Ser Tyr Ser Lys
        35                  40                  45

Ala Glu Trp Ser Asp Ser Ala Gln Gly Ser Glu Ser His Ser Leu
    50                  55                  60

<210> SEQ ID NO 26
<211> LENGTH: 72
<212> TYPE: DNA

```
<213> ORGANISM: Artificial Sequence
<220> FEATURE:
<223> OTHER INFORMATION: Description of Artificial Sequence: Synthetic
      chimeric sequence Reformed SP

<400> SEQUENCE: 26
atggcggtca tggcgccccg aaccctcgtc ctgctactct cgggggccct gaccctgacc      60
gagacctggg cg                                                          72

<210> SEQ ID NO 27
<211> LENGTH: 270
<212> TYPE: DNA
<213> ORGANISM: Artificial Sequence
<220> FEATURE:
<223> OTHER INFORMATION: Description of Artificial Sequence: Synthetic
      chimeric sequence a1 domain

<400> SEQUENCE: 27
ggctcccact ccttgaagta tttccacact tccgtgtccc ggcccggccg cggggagccc      60
cgcttcatct ctgtgggcta cgtggacgac acccagttcg tgcgcttcga caacgacgcc     120
gcgagtccga ggatggtgcc gcgggcgccg tggatggagc aggagggtc agagtattgg      180 gaccgggaga cacggagcgc cagggacacc gcacagattt ccgagtgaa tctgcggacg      240 ctgcgcggct actacaatca gagcgaggcc                                      270

<210> SEQ ID NO 28
<211> LENGTH: 276
<212> TYPE: DNA
<213> ORGANISM: Artificial Sequence
<220> FEATURE:
<223> OTHER INFORMATION: Description of Artificial Sequence: Synthetic
      chimeric sequence a2 domain

<400> SEQUENCE: 28
agttctcaca ccctccagtg gatgattggc tgcgacctgg ggtccgacgg tcgcctcctc      60
cgcgggtatg aacagtatgc ctacgatggc aaggattacc tcgccctgaa cgaggacctg     120
cgctcctgga ccgcagcgga cactgcggct cagatctcca agcgcaagtg tgaggcggcc     180
aatgtggctg aacaaaggag agcctacctg gagggcacgt gcgtggagtg gctccacaga     240
tacctggaga acgggaagga gatgctgcag cgcgcg                               276

<210> SEQ ID NO 29
<211> LENGTH: 276
<212> TYPE: DNA
<213> ORGANISM: Artificial Sequence
<220> FEATURE:
<223> OTHER INFORMATION: Description of Artificial Sequence: Synthetic
      chimeric sequence a3 domain

<400> SEQUENCE: 29
gagcccccaa agacacacgt gactcaccac cccatctctg accatgaggc caccctgagg      60
tgctgggccc tgggcttcta ccctgcggag atcacactga cctggcagca ggatggggag     120
ggccataccc aggacacgga gctcgtggag accaggcctg caggggatgg aaccttccag     180
aagtgggcag ctgtggtggt gccttctgga gaggagcaga gatacacgtg ccatgtgcag     240 catgagggc tacccgagcc cgtcaccctg agatgg                                276

<210> SEQ ID NO 30
<211> LENGTH: 192
<212> TYPE: DNA
<213> ORGANISM: Artificial Sequence
```

```
<220> FEATURE:
<223> OTHER INFORMATION: Description of Artificial Sequence:  Synthetic
      chimeric sequence Transmembrane domain

<400> SEQUENCE: 30
aagccggctt cccagcccac catcccatc gtgggcatca ttgctggcct ggttctcctt      60
ggatctgtgg tctctggagc tgtggttgct gctgtgatat ggaggaagaa gagctcaggt     120
ggaaaaggag ggagctactc taaggctgag tggagcgaca gtgcccaggg gtctgagtct    180
cacagcttgt aa                                                         192

<210> SEQ ID NO 31
<211> LENGTH: 24
<212> TYPE: PRT
<213> ORGANISM: Artificial Sequence
<220> FEATURE:
<223> OTHER INFORMATION: Description of Artificial Sequence:  Synthetic
      chimeric sequence Reformed SP

<400> SEQUENCE: 31

Met Ala Val Met Ala Pro Arg Thr Leu Val Leu Leu Leu Ser Gly Ala
1               5                   10                  15

Leu Thr Leu Thr Glu Thr Trp Ala
            20

<210> SEQ ID NO 32
<211> LENGTH: 90
<212> TYPE: PRT
<213> ORGANISM: Artificial Sequence
<220> FEATURE:
<223> OTHER INFORMATION: Description of Artificial Sequence:  Synthetic
      chimeric sequence a1 domain

<400> SEQUENCE: 32

Gly Ser His Ser Leu Lys Tyr Phe His Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Asn Asp Ala Ala Ser Pro Arg Met Val Pro Arg
        35                  40                  45

Ala Pro Trp Met Glu Gln Glu Gly Ser Glu Tyr Trp Asp Arg Glu Thr
    50                  55                  60

Arg Ser Ala Arg Asp Thr Ala Gln Ile Phe Arg Val Asn Leu Arg Thr
65                  70                  75                  80

Leu Arg Gly Tyr Tyr Asn Gln Ser Glu Ala
                85                  90

<210> SEQ ID NO 33
<211> LENGTH: 92
<212> TYPE: PRT
<213> ORGANISM: Artificial Sequence
<220> FEATURE:
<223> OTHER INFORMATION: Description of Artificial Sequence:  Synthetic
      chimeric sequence a2 domain

<400> SEQUENCE: 33

Gly Ser His Thr Leu Gln Trp Met His Gly Cys Glu Leu Gly Pro Asp
1               5                   10                  15

Arg Arg Phe Leu Arg Gly Tyr Glu Gln Phe Ala Tyr Asp Gly Lys Asp
            20                  25                  30

Tyr Leu Thr Leu Asn Glu Asp Leu Arg Ser Trp Thr Ala Val Asp Thr
        35                  40                  45
```

Ala Ala Gln Ile Ser Lys Arg Lys Cys Glu Ala Ala Asn Val Ala Glu
            50                  55                  60

Gln Arg Arg Ala Tyr Leu Glu Gly Thr Cys Val Glu Trp Leu His Arg
65                  70                  75                  80

Tyr Leu Glu Asn Gly Lys Glu Met Leu Gln Arg Ala
                85                  90

<210> SEQ ID NO 34
<211> LENGTH: 92
<212> TYPE: PRT
<213> ORGANISM: Artificial Sequence
<220> FEATURE:
<223> OTHER INFORMATION: Description of Artificial Sequence: Synthetic
      chimeric sequence a3 domain

<400> SEQUENCE: 34

Glu Pro Pro Lys Thr His Val Thr His His Pro Ile Ser Asp His Glu
1               5                   10                  15

Ala Thr Leu Arg Cys Trp Ala Leu Gly Phe Tyr Pro Ala Glu Ile Thr
                20                  25                  30

Leu Thr Trp Gln Gln Asp Gly Glu Gly His Thr Gln Asp Thr Glu Leu
            35                  40                  45

Val Glu Thr Arg Pro Ala Gly Asp Gly Thr Phe Gln Lys Trp Ala Ala
        50                  55                  60

Val Val Val Pro Ser Gly Glu Glu Gln Arg Tyr Thr Cys His Val Gln
65                  70                  75                  80

His Glu Gly Leu Pro Glu Pro Val Thr Leu Arg Trp
                85                  90

<210> SEQ ID NO 35
<211> LENGTH: 63
<212> TYPE: PRT
<213> ORGANISM: Artificial Sequence
<220> FEATURE:
<223> OTHER INFORMATION: Description of Artificial Sequence: Synthetic
      chimeric sequence Transmembrane domain

<400> SEQUENCE: 35

Lys Pro Ala Ser Gln Pro Thr Ile Pro Ile Val Gly Ile Ile Ala Gly
1               5                   10                  15

Leu Val Leu Leu Gly Ser Val Val Ser Gly Ala Val Val Ala Ala Val
                20                  25                  30

Ile Trp Arg Lys Lys Ser Ser Gly Gly Lys Gly Gly Ser Tyr Ser Lys
            35                  40                  45

Ala Glu Trp Ser Asp Ser Ala Gln Gly Ser Glu Ser His Ser Leu
        50                  55                  60

<210> SEQ ID NO 36
<211> LENGTH: 72
<212> TYPE: DNA
<213> ORGANISM: Artificial Sequence
<220> FEATURE:
<223> OTHER INFORMATION: Description of Artificial Sequence: Synthetic
      chimeric sequence Reformed SP

<400> SEQUENCE: 36
atggcggtca tggcgcccg aaccctcgtc ctgctactct cgggggccct gaccctgacc     60
gagacctggg cg                                                        72

<210> SEQ ID NO 37

<211> LENGTH: 270
<212> TYPE: DNA
<213> ORGANISM: Artificial Sequence
<220> FEATURE:
<223> OTHER INFORMATION: Description of Artificial Sequence: Synthetic chimeric sequence a1 domain

<400> SEQUENCE: 37

| | |
|---|---|
| ggctcccact ccttgaagta tttccacact tccgtgtccc ggcccggccg cggggagccc | 60 |
| cgcttcatct ctgtgggcta cgtggacgac acccagttcg tgcgcttcga caacgacgcc | 120 |
| gcgagtccga ggatggtgcc gcgggcgccg tggatggagc aggaggggtc agagtattgg | 180 |
| gaccgggaga cacggagcgc cagggacacc gcacagattt ccgagtgaa tctgcggacg | 240 |
| ctgcgcggct actacaatca gagcgaggcc | 270 |

<210> SEQ ID NO 38
<211> LENGTH: 276
<212> TYPE: DNA
<213> ORGANISM: Artificial Sequence
<220> FEATURE:
<223> OTHER INFORMATION: Description of Artificial Sequence: Synthetic chimeric sequence a2 domain

<400> SEQUENCE: 38

| | |
|---|---|
| gggtctcaca ccctgcagtg gatgcatggc tgcgagctgg ggcccgacag gcgcttcctc | 60 |
| cgcgggtatg aacagttcgc ctacgacggc aaggattatc tcaccctgaa tgaggacctg | 120 |
| cgctcctgga ccgcggtgga cactgcggct cagatctcca agcgcaagtg tgaggcggcc | 180 |
| aatgtggctg aacaaaggag agcctacctg gagggcacgt gcgtggagtg gctccacaga | 240 |
| tacctggaga acgggaagga gatgctgcag cgcgcg | 276 |

<210> SEQ ID NO 39
<211> LENGTH: 276
<212> TYPE: DNA
<213> ORGANISM: Artificial Sequence
<220> FEATURE:
<223> OTHER INFORMATION: Description of Artificial Sequence: Synthetic chimeric sequence a3 domain

<400> SEQUENCE: 39

| | |
|---|---|
| gagcccccaa agacacacgt gactcaccac cccatctctg accatgaggc caccctgagg | 60 |
| tgctgggccc tgggcttcta ccctgcggag atcacactga cctggcagca ggatggggag | 120 |
| ggccataccc aggacacgga gctcgtggag accaggcctg caggggatgg aaccttccag | 180 |
| aagtgggcag ctgtggtggt gccttctgga gaggagcaga gatacacgtg ccatgtgcag | 240 |
| catgaggggc tacccgagcc cgtcaccctg agatgg | 276 |

<210> SEQ ID NO 40
<211> LENGTH: 192
<212> TYPE: DNA
<213> ORGANISM: Artificial Sequence
<220> FEATURE:
<223> OTHER INFORMATION: Description of Artificial Sequence: Synthetic chimeric sequence Transmembrane domain

<400> SEQUENCE: 40

| | |
|---|---|
| aagccggctt cccagcccac catccccatc gtgggcatca ttgctggcct ggttctcctt | 60 |
| ggatctgtgg tctctggagc tgtggttgct gctgtgatat ggaggaagaa gagctcaggt | 120 |
| ggaaaaggag ggagctactc taaggctgag tggagcgaca gtgcccaggg gtctgagtct | 180 |
| cacagcttgt aa | 192 |

<210> SEQ ID NO 41
<211> LENGTH: 24
<212> TYPE: PRT
<213> ORGANISM: Artificial Sequence
<220> FEATURE:
<223> OTHER INFORMATION: Description of Artificial Sequence: Synthetic
    chimeric sequence Reformed SP

<400> SEQUENCE: 41

Met Ala Val Met Ala Pro Arg Thr Leu Val Leu Leu Leu Ser Gly Ala
1               5                   10                  15

Leu Thr Leu Thr Glu Thr Trp Ala
            20

<210> SEQ ID NO 42
<211> LENGTH: 90
<212> TYPE: PRT
<213> ORGANISM: Artificial Sequence
<220> FEATURE:
<223> OTHER INFORMATION: Description of Artificial Sequence: Synthetic
    chimeric sequence a1 domain

<400> SEQUENCE: 42

Gly Ser His Ser Leu Lys Tyr Phe His Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Asn Asp Ala Ala Ser Pro Arg Met Val Pro Arg
        35                  40                  45

Ala Pro Trp Met Glu Gln Glu Gly Ser Glu Tyr Trp Asp Arg Glu Thr
    50                  55                  60

Arg Ser Ala Arg Asp Thr Ala Gln Ile Phe Arg Val Asn Leu Arg Thr
65                  70                  75                  80

Leu Arg Gly Tyr Tyr Asn Gln Ser Glu Ala
                85                  90

<210> SEQ ID NO 43
<211> LENGTH: 92
<212> TYPE: PRT
<213> ORGANISM: Artificial Sequence
<220> FEATURE:
<223> OTHER INFORMATION: Description of Artificial Sequence: Synthetic
    chimeric sequence a2 domain

<400> SEQUENCE: 43

Gly Ser His Thr Leu Gln Trp Met His Gly Cys Glu Leu Gly Pro Asp
1               5                   10                  15

Arg Arg Phe Leu Arg Gly Tyr Glu Gln Phe Ala Tyr Asp Gly Lys Asp
            20                  25                  30

Tyr Leu Thr Leu Asn Glu Asp Leu Arg Ser Trp Thr Ala Val Asp Thr
        35                  40                  45

Ala Ala Gln Ile Ser Lys Arg Lys Cys Glu Ala Ala Ser Glu Ala Glu
    50                  55                  60

His Gln Arg Ala Tyr Leu Glu Asp Thr Cys Val Glu Trp Leu His Lys
65                  70                  75                  80

Tyr Leu Glu Lys Gly Lys Glu Thr Leu Leu His Leu
                85                  90

<210> SEQ ID NO 44
<211> LENGTH: 92

<212> TYPE: PRT
<213> ORGANISM: Artificial Sequence
<220> FEATURE:
<223> OTHER INFORMATION: Description of Artificial Sequence: Synthetic
      chimeric sequence a3 domain

<400> SEQUENCE: 44

Glu Pro Pro Lys Thr His Val Thr His Pro Ile Ser Asp His Glu
1               5                   10                  15

Ala Thr Leu Arg Cys Trp Ala Leu Gly Phe Tyr Pro Ala Glu Ile Thr
            20                  25                  30

Leu Thr Trp Gln Gln Asp Gly Glu Gly His Thr Gln Asp Thr Glu Leu
        35                  40                  45

Val Glu Thr Arg Pro Ala Gly Asp Gly Thr Phe Gln Lys Trp Ala Ala
    50                  55                  60

Val Val Val Pro Ser Gly Glu Glu Gln Arg Tyr Thr Cys His Val Gln
65                  70                  75                  80

His Glu Gly Leu Pro Glu Pro Val Thr Leu Arg Trp
                85                  90

<210> SEQ ID NO 45
<211> LENGTH: 63
<212> TYPE: PRT
<213> ORGANISM: Artificial Sequence
<220> FEATURE:
<223> OTHER INFORMATION: Description of Artificial Sequence: Synthetic
      chimeric sequence Transmembrane domain

<400> SEQUENCE: 45

Lys Pro Ala Ser Gln Pro Thr Ile Pro Ile Val Gly Ile Ile Ala Gly
1               5                   10                  15

Leu Val Leu Leu Gly Ser Val Val Ser Gly Ala Val Val Ala Ala Val
            20                  25                  30

Ile Trp Arg Lys Lys Ser Ser Gly Gly Lys Gly Gly Ser Tyr Ser Lys
        35                  40                  45

Ala Glu Trp Ser Asp Ser Ala Gln Gly Ser Glu Ser His Ser Leu
    50                  55                  60

<210> SEQ ID NO 46
<211> LENGTH: 72
<212> TYPE: DNA
<213> ORGANISM: Artificial Sequence
<220> FEATURE:
<223> OTHER INFORMATION: Description of Artificial Sequence: Synthetic
      chimeric sequence Reformed SP

<400> SEQUENCE: 46
atggcggtca tggcgccccg aaccctcgtc ctgctactct cgggggccct gaccctgacc      60
gagacctggg cg                                                         72

<210> SEQ ID NO 47
<211> LENGTH: 270
<212> TYPE: DNA
<213> ORGANISM: Artificial Sequence
<220> FEATURE:
<223> OTHER INFORMATION: Description of Artificial Sequence: Synthetic
      chimeric sequence a1 domain

<400> SEQUENCE: 47 ggctccccact ccttgaagta tttccacact tccgtgtccc ggcccggccg cggggagccc     60
cgcttcatct ctgtgggcta cgtggacgac acccagttcg tgcgcttcga caacgacgcc    120

```
gcgagtccga ggatggtgcc gcgggcgccg tggatggagc aggagggctc agagtattgg      180
gaccgggaga cacggagcgc cagggacacc gcacagattt ccgagtgaa tctgcggacg       240 ctgcgcggct actacaatca gagcgaggcc                                       270
```

<210> SEQ ID NO 48
<211> LENGTH: 276
<212> TYPE: DNA
<213> ORGANISM: Artificial Sequence
<220> FEATURE:
<223> OTHER INFORMATION: Description of Artificial Sequence: Synthetic
      chimeric sequence a2 domain

<400> SEQUENCE: 48

```
gggtctcaca ccctgcagtg gatgcatggc tgcgagctgg ggcccgacag gcgcttcctc      60
cgcgggtatg aacagttcgc ctacgacggc aaggattatc tcaccctgaa tgaggacctg     120
cgctcctgga ccgcggtgga cactgcggct cagatctcca agcgcaagtg tgaggcggcc    180
tctgaggcgg agcaccagag agcctacctg aagacacat gcgtggagtg gctccacaaa    240
tacctggaga aggggaagga gacgctgctt cacctg                               276
```

<210> SEQ ID NO 49
<211> LENGTH: 276
<212> TYPE: DNA
<213> ORGANISM: Artificial Sequence
<220> FEATURE:
<223> OTHER INFORMATION: Description of Artificial Sequence: Synthetic
      chimeric sequence a3 domain

<400> SEQUENCE: 49

```
gagcccccaa agacacacgt gactcaccac cccatctctg accatgaggc caccctgagg      60
tgctgggccc tgggcttcta ccctgcggag atcacactga cctggcagca ggatggggag    120
ggccataccc aggacacgga gctcgtggag accaggcctg caggggatgg aaccttccag    180
aagtgggcag ctgtggtggt gccttctgga gaggagcaga gatacacgtg ccatgtgcag    240
catgaggggc taccccgagcc cgtcaccctg agatgg                              276
```

<210> SEQ ID NO 50
<211> LENGTH: 192
<212> TYPE: DNA
<213> ORGANISM: Artificial Sequence
<220> FEATURE:
<223> OTHER INFORMATION: Description of Artificial Sequence: Synthetic
      chimeric sequence Transmembrane domain

<400> SEQUENCE: 50

```
aagccggctt cccagcccac catccccatc gtgggcatca ttgctggcct ggttctcctt      60
ggatctgtgg tctctggagc tgtggttgct gctgtgatat ggaggaagaa gagctcaggt     120
ggaaaaggag ggagctactc taaggctgag tggagcgaca gtgcccaggg gtctgagtct    180
cacagcttgt aa                                                          192
```

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      chimeric sequence SP of HLA-E

<400> SEQUENCE: 51

Met Val Asp Gly Thr Leu Leu Leu Leu Leu Ser Glu Ala Leu Ala Leu

```
                          1               5                  10                 15
Thr Gln Thr Trp Ala
                 20

<210> SEQ ID NO 52
<211> LENGTH: 90
<212> TYPE: PRT
<213> ORGANISM: Artificial Sequence
<220> FEATURE:
<223> OTHER INFORMATION: Description of Artificial Sequence: Synthetic
      chimeric sequence a1 domain

<400> SEQUENCE: 52

Gly Ser His Ser Leu Lys Tyr Phe His Thr Ser Val Ser Arg Pro Gly
1               5                   10                  15

Arg Gly Glu Pro Arg Phe Ile Ser Val Gly Tyr Val Asp Asp Thr Gln
                20                  25                  30

Phe Val Arg Phe Asp Asn Asp Ala Ala Ser Pro Arg Met Val Pro Arg
            35                  40                  45

Ala Pro Trp Met Glu Gln Glu Gly Ser Glu Tyr Trp Asp Arg Glu Thr
        50                  55                  60

Arg Ser Ala Arg Asp Thr Ala Gln Ile Phe Arg Val Asn Leu Arg Thr
65                  70                  75                  80

Leu Arg Gly Tyr Tyr Asn Gln Ser Glu Ala
                85                  90

<210> SEQ ID NO 53
<211> LENGTH: 92
<212> TYPE: PRT
<213> ORGANISM: Artificial Sequence
<220> FEATURE:
<223> OTHER INFORMATION: Description of Artificial Sequence: Synthetic
      chimeric sequence a2 domain

<400> SEQUENCE: 53

Gly Ser His Thr Leu Gln Trp Met His Gly Cys Glu Leu Gly Pro Asp
1               5                   10                  15

Arg Arg Phe Leu Arg Gly Tyr Glu Gln Phe Ala Tyr Asp Gly Lys Asp
                20                  25                  30

Tyr Leu Thr Leu Asn Glu Asp Leu Arg Ser Trp Thr Ala Val Asp Thr
            35                  40                  45

Ala Ala Gln Ile Ser Glu Gln Lys Cys Asn Asp Ala Ser Glu Ala Glu
        50                  55                  60

His Gln Arg Ala Tyr Leu Glu Asp Thr Cys Val Glu Trp Leu His Lys
65                  70                  75                  80

Tyr Leu Glu Lys Gly Lys Glu Thr Leu Leu His Leu
                85                  90

<210> SEQ ID NO 54
<211> LENGTH: 92
<212> TYPE: PRT
<213> ORGANISM: Artificial Sequence
<220> FEATURE:
<223> OTHER INFORMATION: Description of Artificial Sequence: Synthetic
      chimeric sequence a3 domain

<400> SEQUENCE: 54

Glu Pro Pro Lys Thr His Val Thr His His Pro Ile Ser Asp His Glu
1               5                   10                  15

Ala Thr Leu Arg Cys Trp Ala Leu Gly Phe Tyr Pro Ala Glu Ile Thr
                20                  25                  30
```

Leu Thr Trp Gln Gln Asp Gly Glu Gly His Thr Gln Asp Thr Glu Leu
            35                  40                  45

Val Glu Thr Arg Pro Ala Gly Asp Gly Thr Phe Gln Lys Trp Ala Ala
    50                  55                  60

Val Val Val Pro Ser Gly Glu Glu Gln Arg Tyr Thr Cys His Val Gln
65                  70                  75                  80

His Glu Gly Leu Pro Glu Pro Val Thr Leu Arg Trp
                85                  90

<210> SEQ ID NO 55
<211> LENGTH: 63
<212> TYPE: PRT
<213> ORGANISM: Artificial Sequence
<220> FEATURE:
<223> OTHER INFORMATION: Description of Artificial Sequence: Synthetic
      chimeric sequence Transmembrane domain

<400> SEQUENCE: 55

Lys Pro Ala Ser Gln Pro Thr Ile Pro Ile Val Gly Ile Ile Ala Gly
1               5                   10                  15

Leu Val Leu Leu Gly Ser Val Val Ser Gly Ala Val Val Ala Ala Val
            20                  25                  30

Ile Trp Arg Lys Lys Ser Ser Gly Gly Lys Gly Gly Ser Tyr Ser Lys
        35                  40                  45

Ala Glu Trp Ser Asp Ser Ala Gln Gly Ser Glu Ser His Ser Leu
    50                  55                  60

<210> SEQ ID NO 56
<211> LENGTH: 63
<212> TYPE: DNA
<213> ORGANISM: Artificial Sequence
<220> FEATURE:
<223> OTHER INFORMATION: Description of Artificial Sequence: Synthetic
      chimeric sequence SP of HLA-E

<400> SEQUENCE: 56
atggtagatg aaccctcct tttactcctc tcggaggccc tggcccttac ccagacctgg      60
gcg                                                                   63

<210> SEQ ID NO 57
<211> LENGTH: 270
<212> TYPE: DNA
<213> ORGANISM: Artificial Sequence
<220> FEATURE:
<223> OTHER INFORMATION: Description of Artificial Sequence: Synthetic
      chimeric sequence a1 domain

<400> SEQUENCE: 57
ggctcccact ccttgaagta tttccacact tccgtgtccc ggcccggccg cggggagccc      60
cgcttcatct ctgtgggcta cgtggacgac acccagttcg tgcgcttcga caacgacgcc     120
gcgagtccga ggatggtgcc gcgggcgccg tggatggagc aggagggtc agagtattgg      180 gaccgggaga cacggagcgc cagggacacc gcacagattt tccgagtgaa tctgcggacg     240
ctgcgcggct actacaatca gagcgaggcc                                     270

<210> SEQ ID NO 58
<211> LENGTH: 276
<212> TYPE: DNA
<213> ORGANISM: Artificial Sequence
<220> FEATURE:
<223> OTHER INFORMATION: Description of Artificial Sequence: Synthetic -continued chimeric sequence a2 domain

<400> SEQUENCE: 58
gggtctcaca ccctgcagtg gatgcatggc tgcgagctgg ggcccgacag gcgcttcctc    60
cgcgggtatg aacagttcgc ctacgacggc aaggattatc tcaccctgaa tgaggacctg   120
cgctcctgga ccgcggtgga cacggcggct cagatctccg agcaaaagtg taatgatgcc   180
tctgaggcgg agcaccagag agcctacctg gaagacacat gcgtggagtg gctccacaaa   240
tacctggaga aggggaagga gacgctgctt cacctg                             276

<210> SEQ ID NO 59
<211> LENGTH: 276
<212> TYPE: DNA
<213> ORGANISM: Artificial Sequence
<220> FEATURE:
<223> OTHER INFORMATION: Description of Artificial Sequence: Synthetic
      chimeric sequence a3 domain

<400> SEQUENCE: 59
gagcccccaa agacacacgt gactcaccac cccatctctg accatgaggc caccctgagg    60
tgctgggccc tgggcttcta ccctgcggag atcacactga cctggcagca ggatggggag   120
ggccataccc aggacacgga gctcgtggag accaggcctg caggggatgg aaccttccag   180
aagtgggcag ctgtggtggt gccttctgga gaggagcaga gatacacgtg ccatgtgcag   240
catgaggggc tacccgagcc cgtcaccctg agatgg                             276

<210> SEQ ID NO 60
<211> LENGTH: 192
<212> TYPE: DNA
<213> ORGANISM: Artificial Sequence
<220> FEATURE:
<223> OTHER INFORMATION: Description of Artificial Sequence: Synthetic
      chimeric sequence Transmembrane domain

<400> SEQUENCE: 60
aagccggctt cccagcccac catccccatc gtgggcatca ttgctggcct ggttctcctt    60
ggatctgtgg tctctggagc tgtggttgct gctgtgatat ggaggaagaa gagctcaggt   120
ggaaaaggag ggagctactc taaggctgag tggagcgaca gtgcccaggg gtctgagtct   180
cacagcttgt aa                                                       192

<210> SEQ ID NO 61
<211> LENGTH: 24
<212> TYPE: PRT
<213> ORGANISM: Artificial Sequence
<220> FEATURE:
<223> OTHER INFORMATION: Description of Artificial Sequence: Synthetic
      chimeric sequence Reformed SP

<400> SEQUENCE: 61

Met Ala Val Met Ala Pro Arg Thr Leu Val Leu Leu Leu Ser Gly Ala
1               5                   10                  15

Leu Thr Leu Thr Glu Thr Trp Ala
            20

<210> SEQ ID NO 62
<211> LENGTH: 90
<212> TYPE: PRT
<213> ORGANISM: Artificial Sequence
<220> FEATURE:
<223> OTHER INFORMATION: Description of Artificial Sequence: Synthetic
      chimeric sequence a1 domain

<400> SEQUENCE: 62

Gly Ser His Ser Leu Lys Tyr Phe His Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Asn Asp Ala Ala Ser Pro Arg Met Val Pro Arg
        35                  40                  45

Ala Pro Trp Met Glu Gln Glu Gly Ser Glu Tyr Trp Asp Arg Glu Thr
    50                  55                  60

Arg Ser Ala Arg Asp Thr Ala Gln Ile Phe Arg Val Asn Leu Arg Thr
65                  70                  75                  80

Leu Arg Gly Tyr Tyr Asn Gln Ser Glu Ala
                85                  90

<210> SEQ ID NO 63
<211> LENGTH: 92
<212> TYPE: PRT
<213> ORGANISM: Artificial Sequence
<220> FEATURE:
<223> OTHER INFORMATION: Description of Artificial Sequence: Synthetic
      chimeric sequence a2 domain

<400> SEQUENCE: 63

Gly Ser His Thr Leu Gln Trp Met His Gly Cys Glu Leu Gly Pro Asp
1               5                   10                  15

Arg Arg Phe Leu Arg Gly Tyr Glu Gln Phe Ala Tyr Asp Gly Lys Asp
            20                  25                  30

Tyr Leu Thr Leu Asn Glu Asp Leu Arg Ser Trp Thr Ala Val Asp Thr
        35                  40                  45

Ala Ala Gln Ile Ser Glu Gln Lys Cys Asn Asp Ala Ser Glu Ala Glu
    50                  55                  60

His Gln Arg Ala Tyr Leu Glu Asp Thr Cys Val Glu Trp Leu His Lys
65                  70                  75                  80

Tyr Leu Glu Lys Gly Lys Glu Thr Leu Leu His Leu
                85                  90

<210> SEQ ID NO 64
<211> LENGTH: 92
<212> TYPE: PRT
<213> ORGANISM: Artificial Sequence
<220> FEATURE:
<223> OTHER INFORMATION: Description of Artificial Sequence: Synthetic
      chimeric sequence a3 domain

<400> SEQUENCE: 64

Glu Pro Pro Lys Thr His Val Thr His His Pro Ile Ser Asp His Glu
1               5                   10                  15

Ala Thr Leu Arg Cys Trp Ala Leu Gly Phe Tyr Pro Ala Glu Ile Thr
            20                  25                  30

Leu Thr Trp Gln Gln Asp Gly Glu Gly His Thr Gln Asp Thr Glu Leu
        35                  40                  45

Val Glu Thr Arg Pro Ala Gly Asp Gly Thr Phe Gln Lys Trp Ala Ala
    50                  55                  60

Val Val Val Pro Ser Gly Glu Glu Gln Arg Tyr Thr Cys His Val Gln
65                  70                  75                  80

His Glu Gly Leu Pro Glu Pro Val Thr Leu Arg Trp
                85                  90

<210> SEQ ID NO 65
<211> LENGTH: 63
<212> TYPE: PRT
<213> ORGANISM: Artificial Sequence
<220> FEATURE:
<223> OTHER INFORMATION: Description of Artificial Sequence: Synthetic chimeric sequence Transmembrane domain

<400> SEQUENCE: 65

```
Lys Pro Ala Ser Gln Pro Thr Ile Pro Ile Val Gly Ile Ile Ala Gly
1               5                   10                  15

Leu Val Leu Leu Gly Ser Val Val Ser Gly Ala Val Val Ala Ala Val
            20                  25                  30

Ile Trp Arg Lys Lys Ser Ser Gly Gly Lys Gly Gly Ser Tyr Ser Lys
        35                  40                  45

Ala Glu Trp Ser Asp Ser Ala Gln Gly Ser Glu Ser His Ser Leu
    50                  55                  60
```

<210> SEQ ID NO 66
<211> LENGTH: 72
<212> TYPE: DNA
<213> ORGANISM: Artificial Sequence
<220> FEATURE:
<223> OTHER INFORMATION: Description of Artificial Sequence: Synthetic chimeric sequence Reformed SP

<400> SEQUENCE: 66

```
atggcggtca tggcgccccg aaccctcgtc ctgctactct cgggggccct gaccctgacc      60
gagacctggg cg                                                         72
```

<210> SEQ ID NO 67
<211> LENGTH: 270
<212> TYPE: DNA
<213> ORGANISM: Artificial Sequence
<220> FEATURE:
<223> OTHER INFORMATION: Description of Artificial Sequence: Synthetic chimeric sequence a1 domain

<400> SEQUENCE: 67

```
ggctcccact ccttgaagta tttccacact tccgtgtccc ggcccggccg cggggagccc      60
cgcttcatct ctgtgggcta cgtggacgac acccagttcg tgcgcttcga caacgacgcc     120
gcgagtccga ggatggtgcc gcgggcgccg tggatggagc aggaggggtc agagtattgg     180
gaccgggaga cacggagcgc cagggacacc gcacagattt ccgagtgaa tctgcggacg      240 ctgcgcggct actacaatca gagcgaggcc                                     270
```

<210> SEQ ID NO 68
<211> LENGTH: 276
<212> TYPE: DNA
<213> ORGANISM: Artificial Sequence
<220> FEATURE:
<223> OTHER INFORMATION: Description of Artificial Sequence: Synthetic chimeric sequence a2 domain

<400> SEQUENCE: 68

```
gggtctcaca ccctgcagtg gatgcatggc tgcgagctgg ggcccgacag gcgcttcctc      60
cgcgggtatg aacagttcgc ctacgacggc aaggattatc tcaccctgaa tgaggacctg     120
cgctcctgga ccgcggtgga cacggcggct cagatctccg agcaaaagtg taatgatgcc     180
tctgaggcgg agcaccagag agcctacctg aagacacatg cgtggagtg gctccacaaa      240 tacctggaga aggggaagga gacgctgctt cacctg                              276
```

<210> SEQ ID NO 69
<211> LENGTH: 276
<212> TYPE: DNA
<213> ORGANISM: Artificial Sequence
<220> FEATURE:
<223> OTHER INFORMATION: Description of Artificial Sequence: Synthetic chimeric sequence a3 domain

<400> SEQUENCE: 69

```
gagcccccaa agacacacgt gactcaccac cccatctctg accatgaggc caccctgagg      60
tgctgggccc tgggcttcta ccctgcggag atcacactga cctggcagca ggatggggag     120
ggccatacccc aggacacgga gctcgtggag accaggcctg caggggatgg aaccttccag    180
aagtgggcag ctgtggtggt gccttctgga gaggagcaga gatacacgtg ccatgtgcag     240
catgaggggc tacccgagcc cgtcaccctg agatgg                               276
```

<210> SEQ ID NO 70
<211> LENGTH: 192
<212> TYPE: DNA
<213> ORGANISM: Artificial Sequence
<220> FEATURE:
<223> OTHER INFORMATION: Description of Artificial Sequence: Synthetic chimeric sequence Transmembrane domain

<400> SEQUENCE: 70

```
aagccggctt cccagcccac catccccatc gtgggcatca ttgctggcct ggttctcctt      60
ggatctgtgg tctctggagc tgtggttgct gctgtgatat ggaggaagaa gagctcaggt    120
ggaaaaggag ggagctactc taaggctgag tggagcgaca gtgcccaggg gtctgagtct    180
cacagcttgt aa                                                        192
```

<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence: Synthetic chimeric sequence SP of HLA-E

<400> SEQUENCE: 71

Met Val Asp Gly Thr Leu Leu Leu Leu Ser Glu Ala Leu Ala Leu
1               5                   10                  15

Thr Gln Thr Trp Ala
            20

<210> SEQ ID NO 72
<211> LENGTH: 90
<212> TYPE: PRT
<213> ORGANISM: Artificial Sequence
<220> FEATURE:
<223> OTHER INFORMATION: Description of Artificial Sequence: Synthetic chimeric sequence a1 domain

<400> SEQUENCE: 72

Gly Ser His Ser Leu Lys Tyr Phe His Thr Ala Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Asn Asp Ala Ala Ser Pro Arg Met Val Pro Arg
        35                  40                  45

Ala Pro Trp Met Glu Gln Glu Gly Ser Glu Tyr Trp Asp Arg Glu Thr

```
                  50                  55                  60

Arg Ser Ala Arg Asp Thr Ala Gln Ile Phe Arg Val Asn Leu Arg Thr
 65                  70                  75                  80

Leu Arg Gly Tyr Tyr Asn Gln Ser Glu Ala
                 85                  90

<210> SEQ ID NO 73
<211> LENGTH: 92
<212> TYPE: PRT
<213> ORGANISM: Artificial Sequence
<220> FEATURE:
<223> OTHER INFORMATION: Description of Artificial Sequence:  Synthetic
      chimeric sequence a2 domain

<400> SEQUENCE: 73

Gly Ser His Thr Leu Gln Trp Met His Gly Cys Glu Leu Gly Pro Asp
 1               5                  10                  15

Arg Arg Phe Leu Arg Gly Tyr Glu Gln Phe Ala Tyr Asp Gly Lys Asp
                 20                  25                  30

Tyr Leu Thr Leu Asn Glu Asp Leu Arg Ser Trp Thr Ala Val Asp Thr
             35                  40                  45

Ala Ala Gln Ile Ser Glu Gln Lys Cys Asn Asp Ala Ser Glu Ala Glu
         50                  55                  60

His Gln Arg Ala Tyr Leu Glu Asp Thr Cys Val Glu Trp Leu His Lys
 65                  70                  75                  80

Tyr Leu Glu Lys Gly Lys Glu Thr Leu Leu His Leu
                 85                  90

<210> SEQ ID NO 74
<211> LENGTH: 92
<212> TYPE: PRT
<213> ORGANISM: Artificial Sequence
<220> FEATURE:
<223> OTHER INFORMATION: Description of Artificial Sequence:  Synthetic
      chimeric sequence a3 domain

<400> SEQUENCE: 74

Glu Pro Pro Lys Thr His Val Thr His His Pro Ile Ser Asp His Glu
 1               5                  10                  15

Ala Thr Leu Arg Cys Trp Ala Leu Gly Phe Tyr Pro Ala Glu Ile Thr
                 20                  25                  30

Leu Thr Trp Gln Gln Asp Gly Glu Gly His Thr Gln Asp Thr Glu Leu
             35                  40                  45

Val Glu Thr Arg Pro Ala Gly Asp Gly Thr Phe Gln Lys Trp Ala Ala
         50                  55                  60

Val Val Val Pro Ser Gly Glu Glu Gln Arg Tyr Thr Cys His Val Gln
 65                  70                  75                  80

His Glu Gly Leu Pro Glu Pro Val Thr Leu Arg Trp
                 85                  90

<210> SEQ ID NO 75
<211> LENGTH: 63
<212> TYPE: PRT
<213> ORGANISM: Artificial Sequence
<220> FEATURE:
<223> OTHER INFORMATION: Description of Artificial Sequence:  Synthetic
      chimeric sequence Transmembrane domain

<400> SEQUENCE: 75

Lys Pro Ala Ser Gln Pro Thr Ile Pro Ile Val Gly Ile Ile Ala Gly
 1               5                  10                  15
```

-continued

```
Leu Val Leu Leu Gly Ser Val Ser Gly Ala Val Val Ala Ala Val
            20                  25                  30

Ile Trp Arg Lys Lys Ser Ser Gly Gly Lys Gly Ser Tyr Ser Lys
        35                  40                  45

Ala Glu Trp Ser Asp Ser Ala Gln Gly Ser Glu Ser His Ser Leu
    50                  55                  60

<210> SEQ ID NO 76
<211> LENGTH: 63
<212> TYPE: DNA
<213> ORGANISM: Artificial Sequence
<220> FEATURE:
<223> OTHER INFORMATION: Description of Artificial Sequence:  Synthetic
      chimeric sequence SP of HLA-E

<400> SEQUENCE: 76
atggtagatg gaaccctcct tttactcctc tcggaggccc tggcccttac ccagacctgg      60
gcg                                                                    63

<210> SEQ ID NO 77
<211> LENGTH: 270
<212> TYPE: DNA
<213> ORGANISM: Artificial Sequence
<220> FEATURE:
<223> OTHER INFORMATION: Description of Artificial Sequence:  Synthetic
      chimeric sequence a1 domain

<400> SEQUENCE: 77
ggctcccact ccttgaagta tttccacact gccgtgtccc ggcccggccg cggggagccc      60
cgcttcatct ctgtgggcta cgtggacgac acccagttcg tgcgcttcga caacgacgcc     120
gcgagtccga ggatggtgcc gcgggcgccg tggatggagc aggagggggtc agagtattgg    180 gaccgggaga cacggagcgc cagggacacc gcacagattt tccgagtgaa tctgcggacg    240
ctgcgcggct actacaatca gagcgaggcc                                      270

<210> SEQ ID NO 78
<211> LENGTH: 276
<212> TYPE: DNA
<213> ORGANISM: Artificial Sequence
<220> FEATURE:
<223> OTHER INFORMATION: Description of Artificial Sequence:  Synthetic
      chimeric sequence a2 domain

<400> SEQUENCE: 78
gggtctcaca ccctgcagtg gatgcatggc tgcgagctgg ggcccgacag gcgcttcctc      60
cgcgggtatg aacagttcgc ctacgacggc aaggattatc tcaccctgaa tgaggacctg     120
cgctcctgga ccgcggtgga cacggcggct cagatctccg agcaaaagtg taatgatgcc    180
tctgaggcgg agcaccagag agcctacctg aagacacat gcgtggagtg gctccacaaa    240
tacctggaga aggggaagga gacgctgctt caccctg                              276

<210> SEQ ID NO 79
<211> LENGTH: 276
<212> TYPE: DNA
<213> ORGANISM: Artificial Sequence
<220> FEATURE:
<223> OTHER INFORMATION: Description of Artificial Sequence:  Synthetic
      chimeric sequence a3 domain

<400> SEQUENCE: 79
gagcccccaa agacacacgt gactcaccac cccatctctg accatgaggc caccctgagg      60
```

```
tgctgggccc tgggcttcta ccctgcggag atcacactga cctggcagca ggatggggag      120
ggccataccc aggacacgga gctcgtggag accaggcctg caggggatgg aaccttccag      180
aagtgggcag ctgtggtggt gccttctgga gaggagcaga gatacacgtg ccatgtgcag      240
catgaggggc tacccgagcc cgtcaccctg agatgg                                276
```

```
<210> SEQ ID NO 80
<211> LENGTH: 192
<212> TYPE: DNA
<213> ORGANISM: Artificial Sequence
<220> FEATURE:
<223> OTHER INFORMATION: Description of Artificial Sequence: Synthetic
      chimeric sequence Transmembrane domain

<400> SEQUENCE: 80
```

```
aagccggctt cccagcccac catccccatc gtgggcatca ttgctggcct ggttctcctt      60
ggatctgtgg tctctggagc tgtggttgct gctgtgatat ggaggaagaa gagctcaggt     120
ggaaaaggag ggagctactc taaggctgag tggagcgaca gtgcccaggg gtctgagtct     180
cacagcttgt aa                                                          192
```

```
<210> SEQ ID NO 81
<211> LENGTH: 24
<212> TYPE: PRT
<213> ORGANISM: Artificial Sequence
<220> FEATURE:
<223> OTHER INFORMATION: Description of Artificial Sequence: Synthetic
      chimeric sequence Reformed SP

<400> SEQUENCE: 81
```

Met Ala Val Met Ala Pro Arg Thr Leu Val Leu Leu Leu Ser Gly Ala
1               5                   10                  15

Leu Thr Leu Thr Glu Thr Trp Ala
            20

```
<210> SEQ ID NO 82
<211> LENGTH: 90
<212> TYPE: PRT
<213> ORGANISM: Artificial Sequence
<220> FEATURE:
<223> OTHER INFORMATION: Description of Artificial Sequence: Synthetic
      chimeric sequence a1 domain

<400> SEQUENCE: 82
```

Gly Ser His Ser Leu Lys Tyr Phe His Thr Ala Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Asn Asp Ala Ala Ser Pro Arg Met Val Pro Arg
        35                  40                  45

Ala Pro Trp Met Glu Gln Glu Gly Ser Glu Tyr Trp Asp Arg Glu Thr
    50                  55                  60

Arg Ser Ala Arg Asp Thr Ala Gln Ile Phe Arg Val Asn Leu Arg Thr
65                  70                  75                  80

Leu Arg Gly Tyr Tyr Asn Gln Ser Glu Ala
                85                  90

```
<210> SEQ ID NO 83
<211> LENGTH: 92
<212> TYPE: PRT
<213> ORGANISM: Artificial Sequence
```

-continued

```
<220> FEATURE:
<223> OTHER INFORMATION: Description of Artificial Sequence:  Synthetic
      chimeric sequence a2 domain

<400> SEQUENCE: 83

Gly Ser His Thr Leu Gln Trp Met His Gly Cys Glu Leu Gly Pro Asp
1               5                  10                  15

Arg Arg Phe Leu Arg Gly Tyr Glu Gln Phe Ala Tyr Asp Gly Lys Asp
            20                  25                  30

Tyr Leu Thr Leu Asn Glu Asp Leu Arg Ser Trp Thr Ala Val Asp Thr
        35                  40                  45

Ala Ala Gln Ile Ser Glu Gln Lys Cys Asn Asp Ala Ser Glu Ala Glu
    50                  55                  60

His Gln Arg Ala Tyr Leu Glu Asp Thr Cys Val Glu Trp Leu His Lys
65                  70                  75                  80

Tyr Leu Glu Lys Gly Lys Glu Thr Leu Leu His Leu
                85                  90

<210> SEQ ID NO 84
<211> LENGTH: 92
<212> TYPE: PRT
<213> ORGANISM: Artificial Sequence
<220> FEATURE:
<223> OTHER INFORMATION: Description of Artificial Sequence:  Synthetic
      chimeric sequence a3 domain

<400> SEQUENCE: 84

Glu Pro Pro Lys Thr His Val Thr His His Pro Ile Ser Asp His Glu
1               5                  10                  15

Ala Thr Leu Arg Cys Trp Ala Leu Gly Phe Tyr Pro Ala Glu Ile Thr
            20                  25                  30

Leu Thr Trp Gln Gln Asp Gly Glu Gly His Thr Gln Asp Thr Glu Leu
        35                  40                  45

Val Glu Thr Arg Pro Ala Gly Asp Gly Thr Phe Gln Lys Trp Ala Ala
    50                  55                  60

Val Val Val Pro Ser Gly Glu Glu Gln Arg Tyr Thr Cys His Val Gln
65                  70                  75                  80

His Glu Gly Leu Pro Glu Pro Val Thr Leu Arg Trp
                85                  90

<210> SEQ ID NO 85
<211> LENGTH: 63
<212> TYPE: PRT
<213> ORGANISM: Artificial Sequence
<220> FEATURE:
<223> OTHER INFORMATION: Description of Artificial Sequence:  Synthetic
      chimeric sequence Transmembrane domain

<400> SEQUENCE: 85

Lys Pro Ala Ser Gln Pro Thr Ile Pro Ile Val Gly Ile Ile Ala Gly
1               5                  10                  15

Leu Val Leu Leu Gly Ser Val Val Ser Gly Ala Val Val Ala Ala Val
            20                  25                  30

Ile Trp Arg Lys Lys Ser Ser Gly Gly Lys Gly Gly Ser Tyr Ser Lys
        35                  40                  45

Ala Glu Trp Ser Asp Ser Ala Gln Gly Ser Glu Ser His Ser Leu
    50                  55                  60

<210> SEQ ID NO 86
<211> LENGTH: 72
```

```
<212> TYPE: DNA
<213> ORGANISM: Artificial Sequence
<220> FEATURE:
<223> OTHER INFORMATION: Description of Artificial Sequence: Synthetic
      chimeric sequence Reformed SP

<400> SEQUENCE: 86
atggcggtca tggcgccccg aaccctcgtc ctgctactct cgggggccct gaccctgacc      60
gagacctggg cg                                                         72

<210> SEQ ID NO 87
<211> LENGTH: 270
<212> TYPE: DNA
<213> ORGANISM: Artificial Sequence
<220> FEATURE:
<223> OTHER INFORMATION: Description of Artificial Sequence: Synthetic
      chimeric sequence a1 domain

<400> SEQUENCE: 87
ggctcccact ccttgaagta tttccacact gccgtgtccc ggcccggccg cggggagccc      60
cgcttcatct ctgtgggcta cgtggacgac acccagttcg tgcgcttcga caacgacgcc     120
gcgagtccga ggatggtgcc gcgggcgccg tggatggagc aggagggtc agagtattgg      180 gaccgggaga cacggagcgc cagggacacc gcacagattt ccgagtgaa tctgcggacg      240 ctgcgcggct actacaatca gagcgaggcc                                     270

<210> SEQ ID NO 88
<211> LENGTH: 276
<212> TYPE: DNA
<213> ORGANISM: Artificial Sequence
<220> FEATURE:
<223> OTHER INFORMATION: Description of Artificial Sequence: Synthetic
      chimeric sequence a2 domain

<400> SEQUENCE: 88
gggtctcaca ccctgcagtg gatgcatggc tgcgagctgg ggcccgacag gcgcttcctc      60
cgcgggtatg aacagttcgc ctacgacggc aaggattatc tcaccctgaa tgaggacctg     120
cgctcctgga ccgcggtgga cacggcggct cagatctccg agcaaaagtg taatgatgcc     180
tctgaggcgg agcaccagag agcctacctg gaagacacat gcgtggagtg gctccacaaa     240
tacctggaga aggggaagga gacgctgctt cacctg                              276

<210> SEQ ID NO 89
<211> LENGTH: 276
<212> TYPE: DNA
<213> ORGANISM: Artificial Sequence
<220> FEATURE:
<223> OTHER INFORMATION: Description of Artificial Sequence: Synthetic
      chimeric sequence a3 domain

<400> SEQUENCE: 89
gagcccccaa agacacacgt gactcaccac cccatctctg accatgaggc caccctgagg      60
tgctgggccc tgggcttcta ccctgcggag atcacactga cctggcagca ggatggggag     120
ggccataccc aggacacgga gctcgtggag accaggcctg caggggatgg aaccttccag     180
aagtgggcag ctgtggtggt gccttctgga gaggagcaga gatacacgtg ccatgtgcag     240
catgaggggc tacccgagcc cgtcaccctg agatgg                              276

<210> SEQ ID NO 90
<211> LENGTH: 192
<212> TYPE: DNA
```

```
<213> ORGANISM: Artificial Sequence
<220> FEATURE:
<223> OTHER INFORMATION: Description of Artificial Sequence: Synthetic
      chimeric sequence Transmembrane domain

<400> SEQUENCE: 90
aagccggctt cccagcccac catccccatc gtgggcatca ttgctggcct ggttctcctt      60
ggatctgtgg tctctggagc tgtggttgct gctgtgatat ggaggaagaa gagctcaggt     120
ggaaaaggag ggagctactc taaggctgag tggagcgaca gtgcccaggg gtctgagtct     180
cacagcttgt aa                                                         192

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      HLA leader peptide

<400> SEQUENCE: 91

Val Met Ala Pro Arg Thr Leu Val Leu
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      HLA leader peptide

<400> SEQUENCE: 92

Val Met Ala Pro Arg Thr Leu Phe Leu
1               5
```

HLA-E CHIMERIC MOLECULE

TECHNICAL FIELD

The present invention relates to HLA-E chimeric molecule. More particularly, it relates to HLA-E chimeric molecules for providing nonhuman mammal cell with resistance to cytotoxicity by human NK cell, base sequences for coding the chimeric molecules, and nonhuman mammal cell and nonhuman mammal animal transformed by the base sequences.

BACKGROUND ART

Organ transplantation is a very useful therapeutic method. Organ transplantation is classified into allotransplantation and xenotransplantation, which have their own merits and demerits. The human-to-human allotransplantation is an established method, but it is limited in the number of donors. Xenotransplantation from nonhuman mammal (for example, swine) to human is multiple in selection of grafts, but it is always accompanied by specific rejections such as hypoacute rejection (HAR) and acute vascular rejection (AVR).

To overcome such specific rejections of xenotransplantation, various methods have been proposed, such as a method of expressing human complement inhibitor in nonhuman mammals (for example, patent document 1), a method of decreasing Galα1,3Gal sequences (hereinafter referred to as α-Gal antigen) of non-reducing terminals of sugar chains not existing in primates or humans but existing in nonhuman mammals (for example, patent document 2), and a method of knocking out genes of α1,3 galactosyl transferase responsible for generation of α-Gal antigen (for example, non-patent documents 1 and 2).

[Patent document 1] Japanese unexamined patent publication No. H11-239430

[Patent document 2] Japanese unexamined patent publication No. 2002-291372

[Non-patent document 1] Science 2002, 295, 1089

[Non-patent document 2] Nat. Biotechnol. 2002, 20, 251

When a graft of nonhuman mammal is transplanted on human recipient, if the HAR can be overcome, the latter's antibody (anti-α-Gal antibody, etc.), complement, platelet, or natural killer (NK) cell may adhere to the former's cell, and the cell may be activated. The activated cell releases various cytokines, dissociates heparin, produces gaps against adjacent cells, exposes collagen of basement membrane, induces blood clotting reaction, closes blood vessels, and necrotizes grafts of nonhuman mammal (non-patent document 3). Such rejections are known as acute vascular rejections (AVR), and so far no method has been known to suppress efficiently the cytotoxicity of NK cell known as one of AVR factors.

[Non-patent document 3] Xenotransplantation 1998, 5, 169

NK cell adheres target cells by way of two types of receptors. They are killer cell activating receptor for inducing cytotoxicity, and killer cell suppressing receptor for suppressing cytotoxicity by recognizing the own MHC class I molecule. When the signal from the former surpasses the signal from the latter, the target cell is necrotized, but when the signal from the latter surpasses the signal from the former, the target cell is not necrotized.

The human cell expresses HLA class I molecules (HLA-A, -B, -C, -E, -F, -G), and hence the human cell is not damaged by human NK cell. On the other hand, sine the nonhuman mammal cell does not express HLA class I molecules, it is damaged by human NK cell. Hence, a new method has been developed to avoid cell damage by human NK cell by transforming the nonhuman mammal cell by genes of human HLA-A, HLA-B, HLA-C, or HLA-G (patent document 3). However, HLA-A, HLA-B, HLA-C are polymorphic, having 175, 344, and 90 alleles respectively, and it is not practical to prepare nonhuman mammal cells applicable to each HLA.

On the other hand, HLA-E and HLA-G are not polymorphic, and it has been attempted to use HLA-E and HLA-G. As a result, it is relatively easy to express HLA-G on the surface of nonhuman mammal cell, but suppression of cytotoxicity by human NK cell is low, and to the contrary it is found not easy to express HLA-E on the surface of nonhuman mammal cell, but suppression of cytotoxicity by human NK cell is high (non-patent document 4).

For the purpose of increasing the HLA-E expressing amount on nonhuman mammal cell surface, it has been attempted to use base sequence for coding the HLA-E, $\beta_2$ microglobulin and HLA-A2 leader peptide (Val-Met-Ala-Pro-Arg-Thr-Leu-Val-Leu) (SEQ ID NO: 91), or base sequence for coding the leader peptide of HLA-G (Val-Met-Ala-Pro-Arg-Thr-Leu-Phe-Leu) (SEQ ID NO: 92). However, the HLA-E expressing amount by these transformants and the suppression of cytotoxicity by NK cell were not sufficient (non-patent document 5).

[Patent document 3] Japanese unexamined patent publication No. H11-510698

[Non-patent document 4] Transplantation Proceedings 2000, 32, 939

[Non-patent document 5] Transplantation 2002, 73, 1582

DISCLOSURE OF THE INVENTION

The invention is devised to solve the problems of the prior art, and the inventors have been intensively studied about HLA-E chimeric molecule for providing the nonhuman mammal cell with resistance to cytotoxicity by human NK cell, and prepared base sequences for coding (1) HLA-E chimeric molecule replacing all or part of α2 domain of HLA-E molecule with all or part of α2 domain of HLA-G1 molecule, (2) HLA-E chimeric molecule replacing, together with (1), signal peptide (SP) of HLA-E molecule with reformed SP partly reforming the SP of HLA-G1 molecule, or (3) HLA-E chimeric molecule replacing, together with (2), part of amino acid sequence of al domain and α2 domain of HLA-E molecule, with part of amino acid sequence of α1 domain and α2 domain of HLA-G1 molecule, respectively, and attempted to transform the nonhuman mammal cell by using them, and found that the expressing amount of HLA-E chimeric molecules is increased and that the resistance to cytotoxicity by human NK cell is increased, thereby completing the invention.

That is, the invention presents HLA-E chimeric molecules for providing nonhuman mammal cell with resistance to cytotoxicity by human NK cell, base sequence for coding them, and nonhuman mammal cells and nonhuman mammal animals transformed by the base sequences.

The reformed SP means a sequence of amino acid sequence of SP in which one or two or more amino acids are replaced or deleted, or one or more amino acids are added, and examples include SP (Met Ala Val Met Ala Pro Arg Thr Leu Val Leu Leu Leu Ser Gly Ala Leu Thr Leu Thr Glu Thr Trp Ala: (SEQ ID NO: 21), hereinafter referred to as reformed SP) by reforming SP (sequence number 11) of HLA-G1 molecule.

Amino acid sequences of signal peptide (SP) of HLA-E molecule, α1 domain, α2 domain, α3 domain and transmembrane (TM) domain are respectively shown in sequence numbers 1 to 5, and their base sequences are shown in sequence numbers 6 to 10.

Amino acid sequences of SP of HLA-G1 molecule, α1 domain, α2 domain, α3 domain and TM domain are respectively shown in sequence numbers 11 to 15, and their base sequences are shown in sequence numbers 16 to 20.

BEST MODE FOR CARRYING OUT THE INVENTION

To achieve the object, the invention presents HLA-E chimeric molecules for providing nonhuman mammal cell with resistance to cytotoxicity by human NK cell, and base sequence for coding them, and more specific examples are chimeric molecules having the following properties and base sequences for coding them.

(1) HLA-E chimeric molecule having reformed SP, being HLA-E chimeric molecule except that amino acid number 91-182 (number from α1 domain N terminal, same hereinafter) of α2 domain of HLA-E molecule is replaced by amino acid number 91-182 of α2 domain of HLA-G1 molecule and a base sequence for coding it. In this chimeric molecule, amino acid sequences of SP, α1 domain, α2 domain, α3 domain, and TM domain are respectively shown in sequence numbers 21 to 25, and their base sequences are respectively shown in sequence numbers 26 to 30;

(2) HLA-E chimeric molecule having reformed SP, being HLA-E chimeric molecule except that amino acid number 137-182 of α2 domain latter part of HLA-E molecule is replaced by amino acid number 137-182 of α2 domain latter part of HLA-G1 molecule and a base sequence for coding it. In this chimeric molecule, amino acid sequences of SP, α1 domain, α2 domain, α3 domain, and TM domain are respectively shown in sequence numbers 31 to 35, and their base sequences are respectively shown in sequence numbers 36 to 40;

(3) HLA-E chimeric molecule having reformed SP, being HLA-E chimeric molecule except that fore part amino acid number 137-150 of α2 domain latter part of HLA-E molecule is replaced by fore part amino acid number 137-150 of α2 domain latter part of HLA-G1 molecule and a base sequence for coding it. In this chimeric molecule, amino acid sequences of SP, α1 domain, α2 domain, α3 domain, and TM domain are respectively shown in sequence numbers 41 to 45, and their base sequences are respectively shown in sequence numbers 46 to 50;

(4) HLA-E chimeric molecule having SP of HLA-E molecule or reformed SP, being HLA-E chimeric molecule except that amino acid number 147 of α2 domain of HLA-E molecule is replaced by cysteine and a base sequence for coding it. In this chimeric molecule, amino acid sequences of SP, α1 domain, α2 domain, α3 domain, and TM domain of chimeric molecule having SP of HLA-E molecule are respectively shown in sequence numbers 51 to 55, their base sequences are respectively shown in sequence numbers 56 to 60, and amino acid sequences of SP, α1 domain, α2 domain, α3 domain, and TM domain of chimeric molecule having reformed SP are respectively shown in sequence numbers 61 to 65, and their base sequences are respectively shown in sequence numbers 66 to 70;

(5) HLA-E chimeric molecule having SP of HLA-E molecule or reformed SP, being HLA-E chimeric molecule except that amino acid number 11 of α1 domain of HLA-E molecule is replaced by alanine, and that amino acid number 147 of α2 domain is replaced by cysteine and a base sequence for coding it. In this chimeric molecule, amino acid sequences of SP, α1 domain, α2 domain, α3 domain, and TM domain of chimeric molecule having SP of HLA-E molecule are respectively shown in sequence numbers 71 to 75, their base sequences are respectively shown in sequence numbers 76 to 80, and amino acid sequences of SP, α1 domain, α2 domain, α3 domain, and TM domain of chimeric molecule having reformed SP are respectively shown in sequence numbers 81 to 85, and their base sequences are respectively shown in sequence numbers 86 to 90; and (6) Nonhuman mammal cell or nonhuman mammal animal provided with resistance to cytotoxicity by human NK cell, prepared and transformed by one base sequence for coding the HLA-E chimeric molecule in any one of (1) to (5) mentioned above.

The human HLA class I molecule consists of signal peptide (SP), α1 domain, α2 domain, α3 domain, and transmembrane (TM) domain, and further includes $\beta_2$ microglobulin ($\beta_2$m).

The human HLA class I molecule also presents antigenicity by sterically incorporating oligopeptide derived from signal peptide (SP) into the groove formed by α1 domain and α2 domain.

As mention above, it is relatively easy to transform the nonhuman mammal cell by using HLA-G gene, but a suppressing capacity of damage by human NK cell is low. To the contrary, a higher suppressing capacity of damage by human cell NK cell is obtained by transforming the nonhuman mammal cell by using HLA-E gene, but it is not easy to transform. Accordingly, in order to provide the nonhuman mammal cell with resistance to cytotoxicity by human NK cell, it has been attempted to prepare a base sequence for coding the HLA-E chimeric molecule by exchanging domains in the HLA-E molecule and HLA-G1 molecule, transform the cell line of nonhuman mammals, and analyze increase or decrease of expressing intensity by FACS, by using anti-HLA antibody (B9.12.1 Cosmobio). As a result, as shown in Examples below, it is found that the HLA-E expression amount of nonhuman mammal cell is increased when transformed by the base sequence for coding the following HLA-E chimeric molecules, and that the resistance to cytotoxicity by human NK cell is increased.

(1) HLA-E chimeric molecule (see sequence numbers 21 to 30) prepared by replacing SP (sequence number 1) of HLA-E molecule with reformed SP (sequence number 21; reformed SP used in Example below), and replacing α2 domain (amino acid number 91-182) of HLA-E molecule with α2 domain (amino acid number 91-182) of HLA-G1 molecule, (2) HLA-E chimeric molecule (see sequence numbers 31 to 40) prepared by replacing SP of HLA-E molecule with the reformed SP, and replacing latter part (amino acid number 137-182) of α2 domain of HLA-E molecule with latter part (amino acid number 137-182) of α2 domain of HLA-G1 molecule, (3) HLA-E chimeric molecule (see sequence numbers 41 to 50) prepared by replacing SP of HLA-E molecule with the reformed SP, and replacing fore part (amino acid number 137-150) of latter part of α2 domain of HLA-E molecule with fore part (amino acid number 137-150) of latter part of α2 domain of HLA-G1 molecule, (4) HLA-E chimeric molecule (see sequence numbers 51 to 60 and sequence numbers 61 to 70) prepared by replacing or not replacing SP of HLA-E molecule with the reformed SP, and replacing serine of amino acid number 147 of α2 domain of HLA-E molecule with cysteine of amino acid number 147 of α2 domain of HLA-G1 molecule, and (5) HLA-E chimeric molecule (see sequence numbers 71 to 80 and sequence numbers 81 to 90) prepared by replacing or not replacing SP of HLA-E molecule with the reformed SP, and replacing serine of amino acid number 11 of α1 domain of HLA-E molecule and serine of amino acid number 147 of α2 domain of the same with alanine of amino acid number 11 of α1 of HLA-G1 molecule and cysteine of amino acid number 147 of α2 of the same.

By building up a transgene by using a base sequence for coding one of the HLA-E chimeric molecules of (1) to (5) mentioned above, and gene promoter (for example, β-actin promoter, pMCP promoter, etc.), and/or other expression adjusting sequence, and transforming the nonhuman mammal cell by using the transgenes, it is possible to prepare nonhuman mammal cell having resistance to cytotoxicity by human NK cell.

By injecting the transgene into a fertilized egg of nonhuman mammal by microinjection method, it is possible to prepare nonhuman transgenic mammals composed of cells, tissues and organs having resistance to cytotoxicity by human NK cell. In the invention, nonhuman transgenic mammals are not particularly specified as far as nonhuman, and examples include swine, mouse, rat, hamster, cow, horse, sheep, rabbit, dog and cat, and considering xenotransplantation, swine may be preferred as a donor.

Further, by applying the nuclear-transfer method using the nonhuman mammal cell having resistance to cytotoxicity by human NK cell as donor cells, it is possible to prepare nonhuman cloned mammals composed of cells, tissues and organs having resistance to cytotoxicity by human NK cell. These nonhuman transgenic mammals or nonhuman cloned mammals can be prepared by properly selecting from the known methods and conditions.

INDUSTRIAL APPLICABILITY

The HLA-E chimeric molecule of the invention can be expressed efficiently on nonhuman mammal cells, and the resistance to cytotoxicity by human NK cell can be applied to nonhuman mammal cells. Therefore, the HLA-E chimeric molecule of the invention can effectively prevent generation of cell damage or acute vascular rejection (AVR) by human NK cell caused at the time of xenotransplantation of cells, tissues and organs of nonhuman mammals on human recipients.

EXAMPLES

The invention is more specifically described below by referring to Examples. It must be noted however that the invention is not limited to these Examples alone.

Example 1

Expression of Various HLA-E Chimeric Molecules in Nonhuman Mammal Cell (1)

A base sequence for coding the amino acid sequence composed as shown in Table 1 was incorporated into an expression vector of pCXN (β-actin promoter of chicken, having enhancer of CMV). Each transgene was incorporated into CHO cell, and the relative value of expression amount was determined by FACS analysis by using anti-HLA antibody (Pan-Class I antibody, B9.12.1 Cosmobio). Preparation of expression vector and operation of transfection conformed to the ordinary method of gene recombinant technology (same hereinafter).

Results are shown in Table 1.

TABLE 1

Expression of various HLA-E chimeric molecules in nonhuman mammal cell

| Symbol | | Molecule composition | Expression (relative amount) |
|---|---|---|---|
| (1) | HLA-G1 | HLA-G1 molecule | 100 |
| (2) | HLA-E | HLA-E molecule | <1 |
| (3) | HLA-E(V) | Replaced SP of above (2) by reformed SP | 2 |
| (4) | E(V)-TM | Replaced TM of above (3) by TM of above (1) | 2 |
| (5) | E(V)-α3TM | Replaced α3, TM of above (3) by α3, TM of above (1) | <1 |
| (6) | E(V)-α2 | Replaced α2 of above (3) by α2 of above (1) | 62 |
| (7) | E(V)-α1α3TM | Replaced α1, α3, and TM of above (3) by α1, α3, and TM of above (1) | <1 |
| (8) | E(V)-α1 | Replaced α1 of above (3) by α1 of above (1) | <1 |
| (9) | E(V)-α1-1 | Replaced fore part of α1 of above (3) by fore part of α1 of above (1) | <1 |
| (10) | E(V)-α1-2 | Replaced latter part of α1 of above (3) by latter part of α1 of above (1) | <1 |
| (11) | E(V)-α2-1 | Replaced fore part of α2 of above (3) by fore part of α2 of above (1) | <1 |
| (12) | E(V)-α2-2 | Replaced latter part of α2 of above (3) by latter part of α2 of above (1) | 29 |
| (13) | E(V)-α2-2-1 | Replaced fore part of latter part of α2 of above (3) by fore part of latter part of α2 of above (1) | 26 |
| (14) | E(V)-α2-2-2 | Replaced hind part of latter part of α2 of above (3) by hind part of latter part of α2 of above (1) | 4 |

(Note 1)
Reformed SP: MAVMAPRTLVLLLSGALTLTETWA (SEQ ID NO: 21)

(Note 2)
SP: signal peptide, α1: α1 domain, α2: α2 domain, α3: α3 domain, TM: transmembrane domain As known from the results in Table 1, it is confirmed that the HLA-E chimeric molecule is efficiently expressed on the CHO cell, by replacing the SP sequence of HLA-E molecule by reformed SP (sequence number 21) similar to SP of HLA-G, and replacing α2 domain (amino acid number 91-182) of HLA-E molecule, latter part (amino acid number 137-182) of α2 domain of HLA-E molecule, or fore part (amino acid number 137-150) of latter part of α2 domain of HLA-E molecule respectively by amino acid sequence corresponding to HLA-G1 molecule.

Example 2

Expression of Various HLA-E Chimeric Molecules in Nonhuman Mammal Cell (2)

A base sequence for coding the amino acid sequence composed as shown in Table 2 was incorporated into an expression vector of pCXN. Each transgene was incorporated into CHO cell, and FACS analysis was conducted by using anti-HLA antibody. Results are shown in Table 2.

TABLE 2

Expression of various HLA-E chimeric molecules in nonhuman mammal cell

| Symbol | Molecule composition | Peak of FACS |
|---|---|---|
| (1) Vector | Vector only | 4.94 |
| (2) HLA-E | HLA-E molecule | 15.07 |
| (3) HLA-E(V) | Replaced SP of above (2) by reformed SP | 36.84 |
| (4) HLA-E(147) | Replaced serine of amino acid 147 of α2 domain of above (2) by cysteine | 121.84 |
| (5) HLA-E(V × 147) | Replaced SP of above (4) by reformed SP | 318.97 |

As known from the results in Table 2, it is confirmed that the HLA-E chimeric molecule replacing serine of amino acid number 147 of α2 domain of HLA-E molecule by cysteine of amino acid number 147 of α2 domain of HLA-G1 molecule is efficiently expressed on the CHO cell, and it is also confirmed that the HLA-E chimeric molecule replacing SP sequence of HLA-E molecule by reformed SP (sequence number 21) and replacing the amino acid sequence number 147 of α2 domain of HLA-E molecule by cysteine is more efficiently expressed on the CHO cell. It is further confirmed that the HLA-E chimeric molecule can be more efficiently expressed on the CHO cell by replacing the hydroxyl group (—OH) of β-position of serine by thiol group (—SH) of cysteine.

Example 3

Resistance of Nonhuman Mammal Cell Expressing HLA-E Chimeric Molecule to Cytotoxicity by Human NK Cell A base sequence for coding the amino acid sequence composed as shown in Table 3 was incorporated into an expression vector of pCXN. Each transgene was incorporated into swine endothelial cell (SEC), and stable cell lines were prepared. Human NK-like cells (YT) were applied to transformed SEC cells at a rate of 5:1 (37° C., 4 hours), and lactate dehydrogenase (LDH) released from SEC was detected as index, and the cytotoxicity by human NK cell was measured, and relative value of cytotoxicity was determined. Results are shown in Table 3.

TABLE 3

Resistance of swine endothelia cells to cytotoxicity by human NK cell

| Transformed cell | Description | Cytotoxicity (relative) |
|---|---|---|
| (1) SEC | No gene transduction operation | 100[a] |
| (2) Mock | Transduction of Mock gene | 94[a] |
| (3) HLA-E(V) | Transformation by base sequence of coding HLA-E chimeric molecule replacing SP of HLA-E molecule by reformed SP | 85[b] |
| (4) HLA-E(V, 147) | Transformation by base sequence of coding HLA-E chimeric molecule replacing SP of HLA-E molecule by reformed SP, and replacing amino acid 147 of α2 domain of HLA-E molecule by cysteine | 35[c] |
| (5) HLA-E(V, 11, 147) | Transformation by base sequence of coding HLA-E chimeric molecule replacing amino acid 11 of α1 domain by alanine, in addition to above (4) | 21[d] |

(Note)
[a, b, c, d]There is significant difference among groups identified with different superscripts ($P < 0.05$).

As known from the results in Table 3, it is confirmed that cytotoxicity by human NK cell can be suppressed in swine endothelia cell transformed by base sequence for coding any one of HLA-E chimeric molecule replacing SP of HLA-E molecule by reformed SP; HLA-E chimeric molecule replacing SP of HLA-E molecule by reformed SP and replacing amino acid number 147 of α2 domain of HLA-E molecule by cysteine; and HLA-E chimeric molecule replacing amino acid number 11 of α1 domain by alanine in addition to the above.

The invention claimed is:

1. An HLA-E chimeric molecule that when expressed in a nonhuman mammal cell, is expressed at the cell surface and that possesses one of the following amino acid sequences:
   (1) an HLA-E chimeric molecule wherein the signal peptide (SP) of an HLA-E molecule has been replaced with a reformed SP, wherein the sequence of the reformed SP is SEQ ID NO:21, and the serine corresponding to amino acid 57 of SEQ ID NO: 3 of the α2 domain of the HLA-E molecule has been replaced with cysteine,
   (2) an HLA-E chimeric molecule wherein the signal peptide (SP) of an HLA-E molecule has been replaced with a reformed SP, wherein the sequence of the reformed SP is SEQ ID NO:21, the serine corresponding to amino acid 11 of SEQ ID NO:2 of the α1 domain of the HLA-E molecule has been replaced with alanine; and the serine corresponding to amino acid 57 of SEQ ID NO: 3 of the α2 domain of the HLA-E molecule has been replaced with cysteine, and
   (3) an HLA-E chimeric molecule wherein the signal peptide (SP) of an HLA-E molecule has been replaced with a reformed SP, wherein the sequence of the reformed SP is SEQ ID NO: 21, and the first portion of the latter part of the α2 domain of the HLA-E chimeric molecule, corresponding to amino acids 47-60 of SEQ ID NO: 3 has been replaced with the first portion of the latter part of the α2 domain of the HLA-G1 molecule, corresponding to amino acids 47-60 of SEQ ID NO: 13, wherein the amino acid sequences of the signal peptide (SP), α1 domain, α2 domain, α3 domain and transmembrane domain of the HLA-E molecule are SEQ ID NO: 1-5, respectively.

* * * * *